(12) United States Patent
Nemori et al.

(10) Patent No.: US 6,413,734 B1
(45) Date of Patent: Jul. 2, 2002

(54) METHOD FOR JUDGING EFFECTIVENESS OF DRUG HAVING PROTEASE INHIBITORY ACTIVITY

(75) Inventors: Ryoichi Nemori; Hiroshi Kaise, both of Kanagawa; Mikihiro Kusama, Tokyo, all of (JP)

(73) Assignee: Fuji Photo Film Co., LTD, Kanagawa (JP)

( * ) Notice: Subject to any disclaimer, the term of this patent is extended or adjusted under 35 U.S.C. 154(b) by 152 days.

(21) Appl. No.: 09/641,349

(22) Filed: Aug. 18, 2000

(30) Foreign Application Priority Data

Aug. 18, 1999 (JP) .............................. 11-231424

(51) Int. Cl.[7] .............................. C12Q 1/37; C12Q 1/00; G01N 33/53; A61K 49/00
(52) U.S. Cl. ............................... 435/23; 435/24; 435/4; 435/968; 424/9.2
(58) Field of Search .............................. 435/23, 24, 4, 435/968; 424/9.2

(56) References Cited

U.S. PATENT DOCUMENTS

| 5,853,977 A | 12/1998 | Dalie et al. ..................... 435/4 |
| 5,990,112 A | * 11/1999 | Campbell et al. ........... 514/255 |

FOREIGN PATENT DOCUMENTS

| EP | 0884393 | 12/1998 | |
| JP | WO/9732035 | 9/1997 | ............ C12Q/1/37 |
| RU | 1178761 | 9/1985 | |
| WO | WO 98/11238 | 3/1998 | |
| WO | WO 99/50443 | 10/1999 | |

OTHER PUBLICATIONS

Zorina S. Galis, et al., Microscopic Localization of Active Proteases By In Situ Zymography: Detection of Matrix Metalloproteinase Activity In Vascular Tissue, Methodology Communication, The FASEB Journal, vol. 9, Jul. 1995, pp. 974–980.

* cited by examiner

*Primary Examiner*—Louise N. Leary
(74) *Attorney, Agent, or Firm*—Sughrue Mion, PLLC

(57) ABSTRACT

A method for judging effectiveness of a drug having protease inhibitory activity, which comprises the steps of: (1) bringing a biosample isolated or collected from a patient with a disease in which participation of a protease is suspected into contact with a thin membrane containing a protease substrate and formed on a surface of a support; (2) detecting a trace of digestion formed on the thin membrane by action of a protease; and (3) judging that a drug having protease inhibitory activity is effective for the patient when a trace of digestion is formed on the thin membrane. The method enables accurate judgment as to whether or not a drug having protease inhibitory activity is effective for a patient with a disease in which participation of a protease is suspected such as rheumatoid arthritis and cancer before administration of the drug.

9 Claims, No Drawings

US 6,413,734 B1

METHOD FOR JUDGING EFFECTIVENESS OF DRUG HAVING PROTEASE INHIBITORY ACTIVITY

BACKGROUND OF THE INVENTION

1. Field of the Invention

The present invention relates to a method for judging effectiveness of a drug having protease inhibitory activity. More specifically, the present invention relates to a method for judging effectiveness of a drug having protease inhibitory activity prior to administration of the drug for therapeutic treatment of a disease in which protease participation is suspected.

2. Related Art

Various proteases, for example, matrix metalloproteinases (MMP), plasminogen activators (PA), serine proteases such as plasmin and the like, are known to participate in infiltration and metastasis of cancer cells, progress of periodontal diseases such as periodontitis, progress of tissue destruction such as those in rheumatoid arthritis and the like. As methods for quantitative measurement of such proteases, immunoassay methods and immunoblotting methods utilizing antibodies, electrophoretic zymography methods and so forth are known. Further, as a method for measuring protease activity in tissues, there is known the so-called in situ zymography method described in FASEB Journal, Vol. 9, July, pp.974–980, 1995 or WO 97/32035. For a purpose of inhibiting excessive protease activity and thereby suppressing progress of pathological conditions, various drugs having protease inhibitory activity have been developed or are in a process of development.

The protease activities of MMP, plasmin and the like are controlled by expression amounts and activation degrees of those enzymes, as well as by amounts of endogenous inhibitors. It is known that, among diseases in which participation of a protease is suspected, e.g., rheumatoid arthritis, there are significant differences in degrees of protease activity in lesions, even though the diseases exhibit similar clinical symptoms. In some cases, a drug having protease inhibitory activity exhibits marked efficacy, and in other cases clinical symptoms are scarcely improved by administration of a drug having protease inhibitory activity. Therefore, it is clinically very important to accurately measure protease activity in lesions and judge propriety of administration of a drug having protease inhibitory activity. Although the conventionally known immunoassay methods, immunoblotting methods and electrophoretic zymography methods are effective for detection and quantification of proteases, they cannot accurately measure protease activity, per se. Therefore, they cannot be used for the purpose of judging propriety of administration of a drug having protease inhibitory activity.

SUMMARY OF THE INVENTION

An object of the present invention is to provide a method for judging whether or not a drug having protease inhibitory activity is effective for therapeutic treatment of a disease in which participation of protease is suspected before administration of the drug. More specifically, the object of the present invention is to provide a method for judging whether or not a drug having protease inhibitory activity is effective for therapeutic treatment of a disease in which participation of protease is suspected by utilizing the method for measuring protease activity disclosed in WO97/32035.

The inventors of the present invention conducted various studies to achieve the foregoing object. As a result, they found that comprehensive protease activity, including factors such as expression amount and activation of proteases in inflammatory tissues and so forth, was accurately measurable by using the thin membrane comprising gelatin or the like disclosed in WO97/32035, and accurate judgment was possible as to whether or not a drug having protease inhibitory activity was effective for therapeutic treatment of a patient having the protease activity by using the result of the measurement. The present invention was achieved on the basis of these findings.

The present invention thus provides a method for judging effectiveness of a drug having protease inhibitory activity, which comprises the steps of:

(1) bringing a biosample into contact with a thin membrane containing a protease substrate and formed on a surface of a support, wherein said biosample is isolated or collected from a patient with a disease in which participation of a protease is suspected;

(2) detecting a trace of digestion formed on the thin membrane by action of a protease; and (3) judging that a drug having protease inhibitory activity is effective for the patient when the trace of digestion is formed on the thin membrane. In the aforementioned method, when a distinct trace of digestion are not formed on the thin membrane, it is judged that administration of a drug having protease inhibitory activity is not effective for treatment of the patient.

According to another aspect of the present invention, there is provided a method for judging propriety of administration of a drug having protease inhibitory activity to a patient with a disease in which participation of a protease is suspected, which comprises the following steps of:

(1) bringing a biosample isolated or collected from the patient into contact with a thin membrane containing a protease substrate and formed on a surface of a support;

(2) detecting a trace of digestion formed on the thin membrane by action of protease; and (3) judging that a drug having protease inhibitory activity should be administered to the patient when the trace of digestion is formed on the thin membrane.

In the aforementioned methods, participation of a protease can be more accurately determined by bringing a sample substantially the same as that used in the step (1) into contact with a thin membrane containing a protease substrate and a protease inhibitor and formed on a surface of a support and then comparing traces of digestion on the above membrane with the traces of digestion on the thin membrane obtained in the step (1), and thus more accurate judgment can be realized. In this embodiment, it is more preferable to use two or more thin membranes each containing a different protease inhibitor. Furthermore, effectiveness of a drug for treatment of the patient can be more accurately judged by bringing the collected sample into contact with a protease inhibitor beforehand for treatment with the inhibitor, then performing the steps (1) and (2), followed by comparing the result with that obtained from a non-treated sample.

According to preferred embodiments of the aforementioned methods, there are provided the aforementioned method, wherein the biosample is cancer tissue, lymph node, periodontal disease tissue, gingival crevicular exudate, destructive morbid tissue or extract (e.g., synovial fluid of rheumatic morbidity, exudate of alveolar pyorrhea tissue), pleural effusion, ascites, cerebrospinal fluid, bronchial washing fluid, mammary gland abnormal secretion fluid, intraovarian retention fluid, sputum or urine; the aforementioned method, wherein the protease is a matrix metalloproteinase or a serine protease; the aforementioned method, wherein the thin membrane to be used is a gelatin thin membrane, casein thin membrane or collagen thin membrane formed on the surface of the support; the aforementioned method, wherein the thin membrane to be used is a fluorescence-labeled gelatin thin membrane, fluorescence-labeled casein thin membrane or fluorescence-labeled collagen thin membrane formed on the surface of the support; the aforementioned methods wherein the traces of digestion on the thin membrane are detected by staining the membrane with a dye; the aforementioned method wherein the traces of digestion on the thin membrane are detected by a fluorescence microscope; the aforementioned method wherein the traces of digestion on the thin membrane are detected by visual inspection using a microscope; and the aforementioned method wherein quantification or numeration of the traces of digestion is carried out by using an image processing apparatus. Furthermore, the present invention also provides a drug having protease inhibitory activity which is judged to be effective for a patient by the aforementioned method; and a thin membrane used for the aforementioned methods.

By the method of the present invention, accurate judgment is achieved as to whether or not a drug having protease inhibitory activity is effective for a patient with rheumatoid arthritis, cancer or the like in which participation of a protease is suspected. Therefore, an accurate guideline about propriety of administration of the drug is obtainable, and therapeutic efficiency can be improved.

PREFERRED EMBODIMENTS OF THE INVENTION

In the methods of the present invention, the protease substrate in the thin membrane is digested depending on activity of protease contained in a sample, and thereby traces of digestion are formed on the thin membrane depending on the activity of the protease. Such traces of digestion can be detected under a microscope through, for example, change of fluorescence or staining of the thin membrane, and strength of protease activity in a sample can generally be measured by determining size and depth of the traces of digestion by visual inspection. Furthermore, by performing a similar procedure separately on a thin membrane comprising a protease inhibitor (the term "protease inhibitor" used herein includes any substances that have protease inhibitory activity including drugs having inhibitory activity against proteases, for example, a substance having inhibitory activity against matrix metalloproteinase or serine protease is preferred), the kind of the protease which exhibits activity in the sample can be identified, and judgment can be made whether or not a drug having potent inhibitory activity against the protease should be administered to the patient. In addition, by contacting a sample with a drug having protease inhibitory activity and then performing the aforementioned method, it is also possible to judge whether or not the drug should be administered to the patient.

Examples of the protease that can be the object of the present invention include matrix metalloproteinases and serine proteases. These enzymes are explained in detail in "Molecular Mechanism of Cancer Metastasis", Ed. by T. Tsuruo, pp.92–107, Medical View Co., Ltd., 1993. Examples of proteases particularly suitable for the methods of the present invention include, for example, matrix metalloproteinases such as interstitial collagenase (MMP-1), gelatinase A (MMP-2) and gelatinase B (MMP-9); serine proteases such as plasminogen activator (PA) and the like. However, proteases as the objects of the methods of the present invention are not limited to these specific proteases.

The protease substrates are not particularly limited so long as they are macromolecules degradable by a protease as a substrate. For example, collagen, gelatin, proteoglycan, fibronectin, laminin, elastin, casein and the like may be used. Preferably, collagen, gelatin, fibronectin, elastin or casein may be used, and gelatin, casein and collagen are more preferably used. When gelatin is used, a type of gelatin is not particularly limited. For example, alkali extracted bovine bone gelatin, alkali extracted swine cutis gelatin, acid extracted bovine bone gelatin, phthalation-treated bovine bone gelatin, acid extracted swine cutis gelatin and so forth can be used. As the protease substrate, one of the aforementioned substances may be used alone, or two or more of the substrates may be used in combination. Further, in order to facilitate detection of degradation of a substrate by a protease, a protease substrate labeled with a fluorescent dye can be used. A type of the fluorescent dye is not particularly limited, and for example, fluorescein, rhodamine, Texas Red, resorfin, Cy3, Cy5 and the like can be used.

As the thin membrane containing a protease substrate, those described in WO97/32035 can be used. Methods for manufacture and use of the thin membranes, methods for detecting traces of digestion, steps of comparing traces of digestion using a thin membrane containing a protease inhibitor and the like are also specifically disclosed in the aforementioned WO97/32035, of which disclosure is herein incorporated by reference. Performance of the thin membrane may be improved by using a hardening agent, and examples thereof are also disclosed in the aforementioned WO97/32035. A thin membrane having a dry thickness of 0.1 to 10 $\mu$m is preferably used.

As the protease inhibitor, various kinds of chelating agents known to inhibit matrix metalloproteinases, in particular, EDTA or 1,10-phenanthroline can be used. Moreover, as inhibitors specific to matrix proteases, tissue inhibitors of metalloproteinases (TIMP), Batimastat, Marimastat, CGS27023A and other inhibitors can be used. These inhibitors are described in, for example, Sosiki Baiyou Kogaku (The Tissue Culture Engineering), Vol. 25, p.356, 1999. As serine protease inhibitors, phenylmethanesulfonyl fluoride, plasminogen activator inhibitor 1 and the like can be used. These inhibitors are described in "Protease and Biological Mechanism" (Gendai Kagaku [Modern Chemistry], Special Edition No. 22), p.224, 1993. However, the inhibitors are not limited to these compounds.

As samples used for the methods of the present invention, for example, biosamples isolated or collected from a patient may be used. Examples of usable biosamples include, for example, cancer tissues or lymph nodes isolated or collected by surgical operation or histological examination from tumor tissues such as lung cancer, stomach cancer, esophageal cancer, colon cancer, breast cancer, uterine cancer, ovarian cancer, thyroid cancer, liver cancer, intraoral cancer, prostatic cancer, renal cancer, bladder cancer and the like, tissues of periodontal diseases, tissues such as synovial membrane and bone tissue isolated or collected from tissues of rheumatoid arthritis by surgical operation or histological examination, gingival crevicular fluids, fluids contained in destructive morbid tissues (e.g., synovial fluid of rheumatic morbidity, exudate of alveolar pyorrhea tissue), pleural effusions, ascites, cerebrospinal fluids, mammary gland abnormal secretion fluids, ovarian retention fluids, sputum, blood or the like.

When the sample is a tissue, for example, a slice having a thickness of 1 to 10 $\mu$m, preferably 4 to 6 $\mu$m, may be prepared from a sample rapidly frozen in liquid nitrogen by using a cryostat, and then the slice may be applied to a thin membrane so as to bring the sample into contact with the thin membrane. A tissue specimen collected by paracentesis and suction may also be rapidly frozen with a compound and made into slices in a similar manner for use. When a tissue specimen collected by paracentesis and suction is subjected to cytological examination, sucked specimen may be discharged on a thin membrane containing a protease substrate so that the specimen can adhere to the membrane in a dispersed state to allow the sample contact with the thin membrane. Furthermore, as for a tissue specimen, moisture of a collected tissue may be gently wiped, and then the tissue can be pressed softly on a thin membrane containing a protease substrate to allow the sample contact with the thin membrane. An endocervical or endometrial mucosal sample may be collected by using a swab or a brush, and then the sample is pressed softly on a thin membrane to transfer the sample onto the thin membrane.

When a liquid sample such as synovial fluid collected from a patient with rheumatoid arthritis is used as a sample, the sample may be diluted to an appropriate concentration or subjected to necessary pretreatment, and then about 1 to 50 μl, preferably about 1 to 20 μl of the sample can be dropped onto the thin membrane. When gingival crevicular fluid of periodontal disease is used as a sample, a piece of filter paper may be inserted into gingival crevice to collect about 5 to 10 μl of gingival crevicular fluid, and the filter paper may be applied to a thin membrane. After the collection of gingival crevicular fluid, the gingival crevicular fluid may be optionally extracted from the filter paper using distilled water or a suitable buffer (for example, 50 mM Tris-HCl, pH 7.5, 10 mM $CaCl_2$, 0.2 M NaCl), and the extract may be dropped onto a thin membrane. When cells contained in blood, urine, mammary gland abnormal secretion fluid, ascites, pleural effusion, sputum and the like are used as a sample, they can be washed by centrifugation and the like, if necessary, and then dispersed and adsorbed on a thin membrane containing a protease substrate by using a cytocentrifuge apparatus.

After a biosample is brought into contact with a thin membrane containing a protease substrate, the membrane is incubated at a temperature suitable for expression of protease activity, e.g., 37° C., under a saturated humid condition for a period required for digestion of a substrate. When a protease is present in the sample, traces of digestion are formed on the thin membrane. For contact between the thin membrane and a biosample, a method comprising application of a part of tissue, a method comprising dropping of liquid sample, a method comprising dispersion of cells for adsorption or the like can be employed. Time required for incubation may vary depending on the kind of a sample, and may preferably be, for example, about 1 to 48 hours, more preferably 6 to 30 hours at 37° C. for a tissue slice or cells, or 0.5 to 24 hours, more preferably about 1 to 16 hours for a liquid sample. The traces of digestion formed on the thin membrane by a protease in the sample can be detected by staining the membrane with a dye, if necessary, and observing the traces by an optical microscope. When a fluorescence-labeled substrate is used, the staining can be omitted, and the membrane, per se, can be conveniently observed under a fluorescence microscope.

Dyes used for staining the thin membrane containing a protease substrate are not particularly limited. For example, the staining can be conducted by using a dye selected from the group consisting of red dyes, orange dyes and yellow dyes. The terms "red", "orange" and "yellow" used herein should be construed in their widest sense, and they should not be interpreted in any limitative way. Such dyes generally have a maximum absorption in the range of 400 nm to 580 nm. As the red dyes, preferred dyes include Acid Red 1 (C.I. 18050), Acid Red 4 (C.I. 14710), Acid Red 8 (C.I. 14900), Acid Red 37 (C.I. 17045), Acid Red 40 (C.I. 18070), Acid Red 44, Acid Red 106 (C.I. 18110), Acid Red 183 (C.I. 18800), Xylidin Ponceau 2R (C.I. 16150), Mordant Red 19, Nitro Red and Ponceau 3R, and Ponceau 3R is particularly preferred. As orange dyes, examples include Methyl Orange, Ethyl Orange, Crocein Orange G, Orange II, Orange G, Acid Orange 8 (C.I. 15575) and Acid Orange 74 (C.I. 18745). As the yellow dyes, Mordant Yellow 10, Mordant Yellow 7, Acid Yellow 99 (C.I. 13900), Acid Yellow 65 (C.I. 14170), Acid Yellow 17 (C.I. 18965) and Nitrazine Yellow (C.I. 14890) can be preferably used.

As the dye, blue dyes can also be used. For example, Amido Black 10B and Coomassie Brilliant Blue can be used. For example, in the method disclosed in WO 97/32035 where gelatin is stained by using Amido Black 10B, gelatin is stained in dark blue, and staining concentration is reduced only in portions where gelatin is digested by the action of a protease to form white patches. When the thin membrane is stained in red with Ponceau 3R, for example, an entire tissue can be observed on the membrane and it is easy to determine microscopically where traces of digestion exist in the tissue, although the maximum absorbance of the thin membrane usually reaches 2 or more. Furthermore, when conventional nuclear staining using hematoxylin or Methyl Green is applied in combination, nuclear morphology and traces of digestion can be simultaneously observed as signals with different color tones under an optical microscope.

For determination of strength of digestion in traces of digestion, applicable methods include, for example, methods utilizing visual inspection under an optical microscope or a fluorescence microscope, method comprising the step of measurement of optical density or fluorescence intensity using a spectrometer, and a method comprising the steps of inputting images obtained by an optical microscope or a fluorescence microscope into a computer, and then numerically analyzing the traces of digestion through image analysis.

According to the method of the present invention, when traces of digestion are observed on the thin membrane containing a protease substrate, it is judged that a protease exists in the sample isolated from a patient, and a drug having protease inhibitory activity is effective for therapeutic treatment of the patient. Kinds of the drugs having protease inhibitory activity, which are the objects of the judgment by the method of the present invention, are not particularly limited, and any drugs can be used so far that they have inhibitory activity against at least one protease and are applicable to mammals including human. When the same procedure is performed with a thin membrane containing a protease inhibitor for comparison, and the size of the traces of digestion is reduced, it can be judged that a drug having protease inhibitory activity is particularly effective for the therapeutic treatment of the patient. On the other hand, when traces of digestion are not substantially observed on the thin membrane containing a protease substrate, or when only a few traces of digestion are formed, it is judged that a drug having protease inhibitory activity cannot exhibit efficacy in the patient, and administration thereof is generally useless.

When two or more thin membranes each containing a different protease inhibitor are used, and when the size of traces of digestion is reduced in a thin membrane containing a certain protease inhibitor, it can be judged that a class of protease which is inhibited by the protease inhibitor contained in the thin membrane is present in the sample, and a drug having inhibitory activity against the class of protease is effective for therapeutic treatment of the patient. Furthermore, when a sample is contacted and treated with a protease inhibitor beforehand and then subjected to the aforementioned steps, and size of traces of digestion are reduced compared with that obtained without the pretreatment, it can be judged that a drug having protease inhibitory activity is effective for therapeutic treatment of the patient. A method for contacting and treating a surgically collected sample with a protease inhibitor beforehand is described in, for example, Cancer Research, 59, pp.467–473, 1999. Although the methods of the present invention are specifically explained above, it should be understood that any methods, which comprise any steps for judging effectiveness of a drug having protease inhibitory activity by using a thin membrane containing a protease substrate, fall within the scope of the present invention.

EXAMPLES

The present invention will be explained more specifically with reference to the following examples. However, the scope of the present invention is not limited to these examples.

Example 1

A breast cancer specimen, which was extracted by surgical operation and frozen, was sliced at −25° C. into slices having a thickness of 4 $\mu$m by using a cryostat, and adhered to a gelatin thin membrane disclosed in WO97/32035. The thickness of gelatin was 7 $\mu$m. This gelatin membrane was incubated at 37° C. for 16 hours under 100% of relative humidity, and then dried in air. A solution obtained by mixing a solution in which Ponceau 3R was dissolved at a concentration of 0.8% in 6% trichloroacetic acid aqueous solution and ethanol at a volume ratio of 3:7 was used as a staining solution. The membrane was immersed in the solution at room temperature for 4 minutes for staining. After the membrane was washed with water for 10 minutes, the membrane was then immersed in a Mayer's hematoxylin solution for 2 minutes for nuclear staining, and further washed with water for 10 minutes and dried in air. After the drying, a Cover Aid Film (Sakura Seiki Co., Ltd.) was adhered to the membrane using xylene to enclose the breast cancer slice. The film was held on a plastic mount and observed under an optical microscope. Gelatin digestion was observed on sites where the cancer cells were present presumably based on the morphology of the nuclei, and thus protease activity was verified. From these results, it was judged that a drug having protease inhibitory activity was effective for the therapeutic treatment of the patient.

When the same test was performed for each of about 20 specimens of breast cancer, the gelatin degradation was not observed in 2 specimens, and it was judged that administration of a drug having protease inhibitory activity was not necessary for these patients. Among the remaining 18 specimens, strong activity was observed in 8 specimens, and weak activity was observed in 10 specimens. For the patients whose specimens gave strong protease activity, it was judged that a drug having protease inhibitory activity should be administered at a daily dose increased up to the upper limit. For the patients whose specimens gave weak activity, it was judged that other therapies may be primarily applied to see progress, and thereafter the administration of a drug be reconsidered.

Example 2

Protease activity of breast cancer specimens, which were extracted by surgical operation and then frozen, was measured in the same manner as Example 1 using gelatin thin membranes containing a matrix metalloproteinase inhibitor (1,10-phenanthroline) disclosed in WO97/32035. Tests were performed for 20 specimens of breast cancer those used in Example 1. Protease activity was suppressed in all specimens, and traces of digestion were hardly observed in all specimens. Judgments were performed in view of the results of Example 1. Since strong MMP activity was expressed in 8 specimens among the 20 specimens tested, it was judged that a drug having MMP inhibitory activity was effective for therapeutic treatment. Since the two specimens showing no protease activity failed to exhibit abnormal expression of MMP activity, it was judged that administration of a drug having MMP inhibitory activity was not necessary. As for patients deriving the remaining 10 specimens where expression of weak MMP activity was observed, it was judged that other therapies may be primarily applied to see progress, and thereafter application of a drug having MMP inhibitory activity be reconsidered.

Example 3

A breast cancer specimen collected by paracentesis and suction was suspended in a phosphate buffer containing 0.5% of polyvinylpyrrolidone, and adhered to a gelatin thin membrane disclosed in WO97/32035 by using a cytospin apparatus of Shandon Co., Ltd. at a speed of 400 rpm. The membrane thickness of gelatin was 7 $\mu$m. The gelatin membrane was incubated at 37° C. for 16 hours under 100% of relative humidity, and then dried in air. A solution in which Ponceau 3R was dissolved at a concentration of 0.8% in 6% trichloroacetic acid aqueous solution was used as a staining solution. The membrane was immersed in the solution at room temperature for 20 seconds for staining. After the membrane was washed with water for 1 minute, the membrane was immersed in a Mayer's hematoxylin solution for 2 minutes for nuclear staining, and then washed with water for 10 minutes and dried in air. After the drying, a Cover Aid Film (Sakura Seiki Co., Ltd.) was adhered to the membrane using xylene to enclose the cell specimen. The film was held on a plastic mount and observed under an optical microscope. Gelatin digestion was observed on sites where the cancer cells were present presumably based on the morphology of the nuclei, and thus protease activity was verified. From these results, it was judged that a drug having protease inhibitory activity was effective for the therapeutic treatment of the patient.

When the same tests were performed for 5 specimens of breast cancer, strong activities were observed in 4 specimen, and weak activity was observed in 1 specimen. For the patients whose specimens gave strong activities, it was judged that a drug having protease inhibitory activity should be administered at a daily dose increased up to the upper limit. For the patient whose specimen gave weak activity, it was judged that other therapies may be primarily applied see progress, and thereafter application of a drug having MMP inhibitory activity be reconsidered.

Example 4

A breast cancer specimen collected by paracentesis and suction was suspended in a phosphate buffer containing 0.5% of polyvinylpyrrolidone and 10 $\mu$g/ml of TIMP-1 (tissue inhibitor of metalloproteinase-1) and TIMP-2, and adhered to a gelatin thin membrane disclosed in WO97/32035 by using a cytospin apparatus of Shandon Co., Ltd. at a speed of 400 rpm. The membrane thickness of gelatin was 7 $\mu$m. The gelatin membrane was incubated at 37° C. for 16 hours under 100% of relative humidity, and dried in air. A solution in which Ponceau 3R was dissolved at a concentration of 0.8% in 6% trichloroacetic acid aqueous solution was used as a staining solution. The membrane was immersed in the solution at room temperature for 20 seconds for staining. After the membrane was washed with water for 1 minute, the membrane was immersed in a Mayer's hematoxylin solution for 2 minutes for nuclear staining, and then washed with water for 10 minutes and dried in air. After the drying, a Cover Aid Film (Sakura Seiki Co., Ltd.) was adhered to the membrane using xylene to enclose the cell specimen. The film was held on a plastic mount and observed under an optical microscope. Gelatin digestion was not observed on sites where the cancer cells were present presumably based on the morphology of the nuclei, which revealed that protease activity was inhibited. When traces of digestion were detected in the same manner except for the treatments with TIMP-1 and TIMP-2 as a control, presence of distinct traces of digestion was observed. From these results, it was judged that a drug having MMP inhibitory activity was effective for the therapeutic treatment of the patient.

When the same tests were performed for 5 specimens of breast cancer, the traces of digestion were hardly observed in all specimens with the TIMP treatments, whereas distinct traces of digestion were observed without the TIMP treatments. From the results mentioned above, in patients deriving the 5 specimens tested were considered that the MMP activity was abnormally expressed in the tumor sites, and it was judged that a drug having MMP inhibitory activity was effective for therapeutic treatment of these patients.

What is claimed is:

1. A method for judging effectiveness of a drug having protease inhibitory activity, which comprises the steps of:
   (1) bringing a biosample isolated or collected from a patient with a disease in which participation of a protease is suspected into contact with a thin membrane containing a protease substrate and formed on a surface of a support;
   (2) detecting a trace of digestion formed on the thin membrane by action of a protease; and
   (3) judging whether a drug having protease inhibitory activity is effective for the patient when a trace of digestion is formed on the thin membrane.

2. The method according to claim 1, wherein the biosample is cancer tissue, lymph node, periodontal disease tissue, gingival crevicular exudate, destructive morbid tissue or extract, pleural effusion, ascites, cerebrospinal fluid, bronchial washing fluid, mammary gland abnormal secretion fluid, intraovarian retention fluid, sputum, or urine.

3. The method according to claim 1, wherein the protease is a matrix metalloproteinase or a serine protease.

4. The method according to claim 1, wherein the thin membrane is a gelatin thin membrane, casein thin membrane, or collagen thin membrane formed on the surface of the support.

5. The method according to claim 1, wherein the thin membrane to be used is a fluorescence-labeled gelatin thin membrane, fluorescence-labeled casein thin membrane, or fluorescence-labeled collagen thin membrane formed on the surface of the support.

6. The method according to claim 1, wherein the collected biosample is brought into contact with a drug having protease inhibitory activity and then the steps (1) to (3) are carried out, and the drug is judged to be effective when the trace of digestion is decreased compared with a result obtained from the biosample not treated with the drug.

7. A method for judging propriety of administration of a drug having protease inhibitory activity to a patient with a disease in which participation of a protease is suspected, which comprises the steps of:
   (1) bringing a biosample isolated or collected from the patient into contact with a thin membrane containing a protease substrate and formed on a surface of a support;
   (2) detecting a trace of digestion formed on the thin membrane by action of protease; and
   (3) judging whether a drug having protease inhibitory activity should be administered to the patient when a trace of digestion is formed on the thin membrane.

8. A method of use of a thin membrane containing a protease substrate and formed on a surface of a support for judging effectiveness of a drug having protease inhibitory activity, which comprises the steps of:
   (1) bringing a biosample isolated or collected from a patient with a disease in which participation of a protease is suspected into contact with a thin membrane containing a protease substrate and formed on a surface of a support;
   (2) detecting a trace of digestion formed on the thin membrane by action of a protease; and
   (3) judging that a drug having protease inhibitory activity is effective for the patient when a trace of digestion is formed on the thin membrane.

9. A method of use of a thin membrane containing a protease substrate and formed on a surface of a support for judging propriety of administration of a drug having protease inhibitory activity to a patient with a disease in which participation of a protease is suspected, which comprises the steps of:
   (1) bringing a biosample isolated or collected from the patient into contact with a thin membrane containing a protease substrate and formed on a surface of a support;
   (2) detecting a trace of digestion formed on the thin membrane by action of protease; and
   (3) judging that a drug having protease inhibitory activity should be administered to the patient when a trace of digestion is formed on the thin membrane.

* * * * *